(12) United States Patent
Komuda et al.

(10) Patent No.: US 12,097,360 B2
(45) Date of Patent: Sep. 24, 2024

(54) SAFETY NEEDLE DEVICE

(71) Applicant: HTL-STREFA S.A., Ozorków (PL)

(72) Inventors: Marcin Komuda, Ozorków (PL);
Marcin Niemiec, Ozorków (PL);
Robert Grzelak, Ozorków (PL);
Robert Osak, Ozorków (PL); Rafal Perlak, Ozorków (PL); Bartlomiej Bialas, Ozorków (PL)

(73) Assignee: HTL-STREFA S.A., Ozorków (PL)

(*) Notice: Subject to any disclaimer, the term of this patent is extended or adjusted under 35 U.S.C. 154(b) by 390 days.

(21) Appl. No.: 17/554,417

(22) Filed: Dec. 17, 2021

(65) Prior Publication Data
US 2022/0203043 A1 Jun. 30, 2022

(30) Foreign Application Priority Data
Dec. 24, 2020 (EP) .................................. 20217305

(51) Int. Cl.
*A61M 5/32* (2006.01)

(52) U.S. Cl.
CPC ........ *A61M 5/3245* (2013.01); *A61M 5/3271* (2013.01); *A61M 2005/3208* (2013.01)

(58) Field of Classification Search
CPC ............................................ A61M 2005/3254
See application file for complete search history.

(56) References Cited

U.S. PATENT DOCUMENTS

| 7,462,168 | B2 * | 12/2008 | Stonehouse | ......... | A61M 5/3272 |
| | | | | | 604/198 |
| 9,623,194 | B2 * | 4/2017 | Srinivasan | .......... | A61M 5/3293 |
| 2014/0107586 | A1 | 4/2014 | Ruan et al. | | |

FOREIGN PATENT DOCUMENTS

| EP | 1949929 | 7/2008 |
| EP | 2883562 | 6/2015 |

(Continued)

OTHER PUBLICATIONS

Extended European Search Report dated Jun. 22, 2021; Application No. EP20217305.0; 7 pages.

(Continued)

*Primary Examiner* — Laura A Bouchelle
(74) *Attorney, Agent, or Firm* — Mark Bandy; Rankin Hill & Clark, LLP (57) ABSTRACT

Safety needle device (1) comprising: a hub (10) configured to be connected to a pen-injector, the hub (10) comprising a lateral wall (11) and an upper wall (12) which define therebetween a cavity (13) extending between the upper wall (12) and an lower aperture (14) able to receive the pen injector; a needle (20) attached to the hub (10), the needle (20) extending along a longitudinal direction (X-X) between a distal end (21), configured for insertion into a patient, and an opposed proximal end (22) configured to be connected to the pen injector, a back-end shield (30) slidable along the longitudinal direction (X-X) within the cavity (13) of the hub (10) and rotatable about the longitudinal direction (X-X), the back-end shield (30) being movable irreversibly from an initial position, before connection of the pen injector to the hub (10), to a locking position, after removal of the pen injector to the hub (10) passing through an intermediate position, an elastic member (40) arranged within the cavity (13) and acting between the upper wall (12) and the back-end shield (30) to urge the back-end shield (30) towards the proximal end (21) of the needle (10) along the longitudinal direction (X-X), a locking arrangement (50) comprising at least a first locking member (60) formed on the back-end shield (30) and at least a second locking member (70) formed on the hub (10), the second locking member (70) cooperating with the first locking member (60) to guide the back-end shield (30) from the initial position to the locking position and to lock the back-end shield (30) in the locking (Continued)

position, the second locking member (70) comprises a passing through guide (71) formed on the lateral wall (11) of the hub (10); the first locking member (60) comprises a protrusion (61) configured to engage the guide (71) and to slide along the guide (71).

13 Claims, 8 Drawing Sheets

(56) References Cited

FOREIGN PATENT DOCUMENTS

| WO | WO2009/102612 | 8/2009 |
| WO | WO2010126432 | 11/2010 |
| WO | WO2020229706 | 11/2020 |

OTHER PUBLICATIONS

International Search Report dated Jun. 25, 2020; Application No. PCT/EP2020/064221; 4 pages.

* cited by examiner

SAFETY NEEDLE DEVICE

FIELD OF INVENTION

The invention relates to the technical field of a medical device, in particular to a protection device able to prevent the user from accidental or intentional injuries with a needle before and after the use of the medical device.

BACKGROUND OF THE INVENTION

Typically, a safety needle device comprises an elongated needle having a first distal end insertable into the patient's skin and a second proximal end insertable into a pen injector for supplying a substance. The needle is embedded in a hub and partially surrounded by a housing fixed to the hub. A known device comprises also a front-end shield and a back-end shield surrounding the needle and moving along the needle to protect the needle end before and after use. The shields are activated by means of spring elements interposed between the hub and the relative shield. The activation of the front-end shield occurs with the injection, while the activation of the back end shield is occurs when coupling of the safety device with a pen injector. Upon activation, the shields pass into a protect configuration that prevent further uses or injuries. In detail, the device comprises locking means able to lock the sliding of the front and back-end shields after use.

For example, in the art elastic clamps engage the back-end shield when it reaches a specific position sliding towards the proximal end of the needle. Other known locking means are flexible tabs formed on the hub that engage the back-end shield to prevent further movements of it after use.

However, the known safety needle devices show some drawbacks. In fact, such devices do not ensure the correct protection to the user from further uses and from accidental injuries. Furthermore, known devices are complex since they require a lot of elements in order to achieve the correct protection of the user, thereby increasing the overall costs of production.

SUMMARY OF THE INVENTION

In this context, the technical task underlying the present invention is to propose a safety needle device which overcomes the drawbacks of the above prior art.

Specifically, it is an object of the present invention to provide a safety needle device able to ensure the protection to the user and at the same time to improve the availability of the device itself and to reduce the complexity of the back-end mechanism.

The technical task set out and the specified objects are substantially achieved by a cooperation of protrusions formed on the back-end shield and passing through guides formed on the hub to guide and lock the back-end shield.

BRIEF DESCRIPTION OF THE DRAWINGS

The present invention will now be described in more detail hereinafter with reference to the accompanying drawings, in which some embodiments of the invention are shown.

DETAILED DESCRIPTION

With reference to FIGS. 1-8, a safety needle device is indicated as a whole by numeral 1. Specifically, the FIGS. 1-8 do not show a front-end mechanism but they are focused on a back-end mechanism Safety needle device 1 can be associated to a pen injector, not shown, containing a substance to inject into a patient or filled by blood withdrawn by the patient.

The safety needle device 1 comprises a hub 10 configured to be connected to the pen injector. The hub 10 comprises a lateral wall 11 and an upper wall 12 which define therebetween a cavity 13. The latest extends between the upper wall 12 and a lower aperture 14 configured to receive the pen injector.

Preferably the hub 10 has an inner surface 10a facing to the cavity 13 and opposed outer surface 10b.

More preferably, the hub 10 comprises retaining means 80 configured to retain the pen injector. The retaining means 80 are formed on the inner surface 10a of the lateral wall 11 near the aperture 14.

According to a preferred embodiment, the hub 10 has a tubular shape with a circular cross section.

The safety needle device 1 comprises a needle 20 attached to the hub 10. The needle 20 extends along a longitudinal direction X-X between a distal end 21, formed to be inserted into a patient, and opposed proximal end 22 formed to be connected to the pen injector.

According to one embodiment, at least a portion of the needle 20 is arranged inside the cavity 13. Preferably, the proximal end 22 of the needle 20 is arranged inside the cavity 13.

The safety needle device 1 comprises a back-end shield 30 slidable along the longitudinal direction X-X within the cavity 30 of the hub 10 and rotatable about the longitudinal direction X-X. Specifically, the back-end shield 30 is slidable and rotatable with respect to the hub 10. Preferably, the back-end shield 30 is movable irreversibly from an initial position, before connection of the pen injector to the hub 10, to a locking position, after removal of the pen injector to the hub 10 passing through an intermediate position. More preferably, during the connection of the hub 10 to the pen injector, the back-end shield 30 passes from the initial position to the intermediate position sliding and rotating towards the distal end 22 of the needle 20 along and about the longitudinal direction X-X. Moreover, during the removal of the pen injector the back-end shield 30 passes from the intermediate position to the locking position sliding and rotating towards the proximal end 21 of the needle 10 along the longitudinal axis X-X.

According to a preferred embodiment, the back-end shield 30 is configured to cover and protect the proximal end 22 of the needle 30 in the locking position. Specifically, the back-end shield 30 is configured to be locked in the locking position avoiding further sliding that would lead to uncovering the proximal end 22 of the needle 20 after use.

Figure 1:
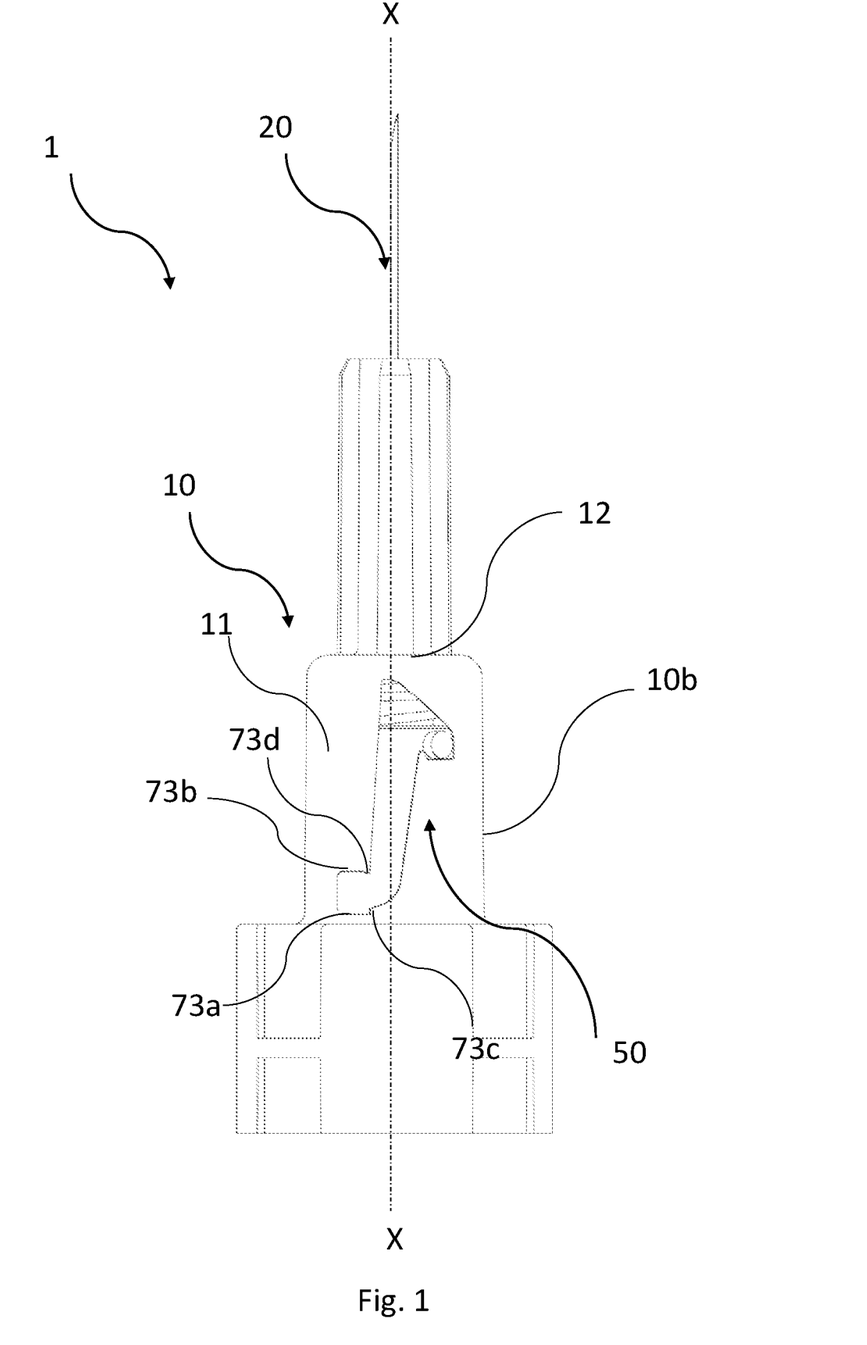
FIG. 1 is a lateral view of the safety needle device according to one embodiment of the present invention, in pre-use configuration, where some elements are hided to better show other aspects.
Figure 2:
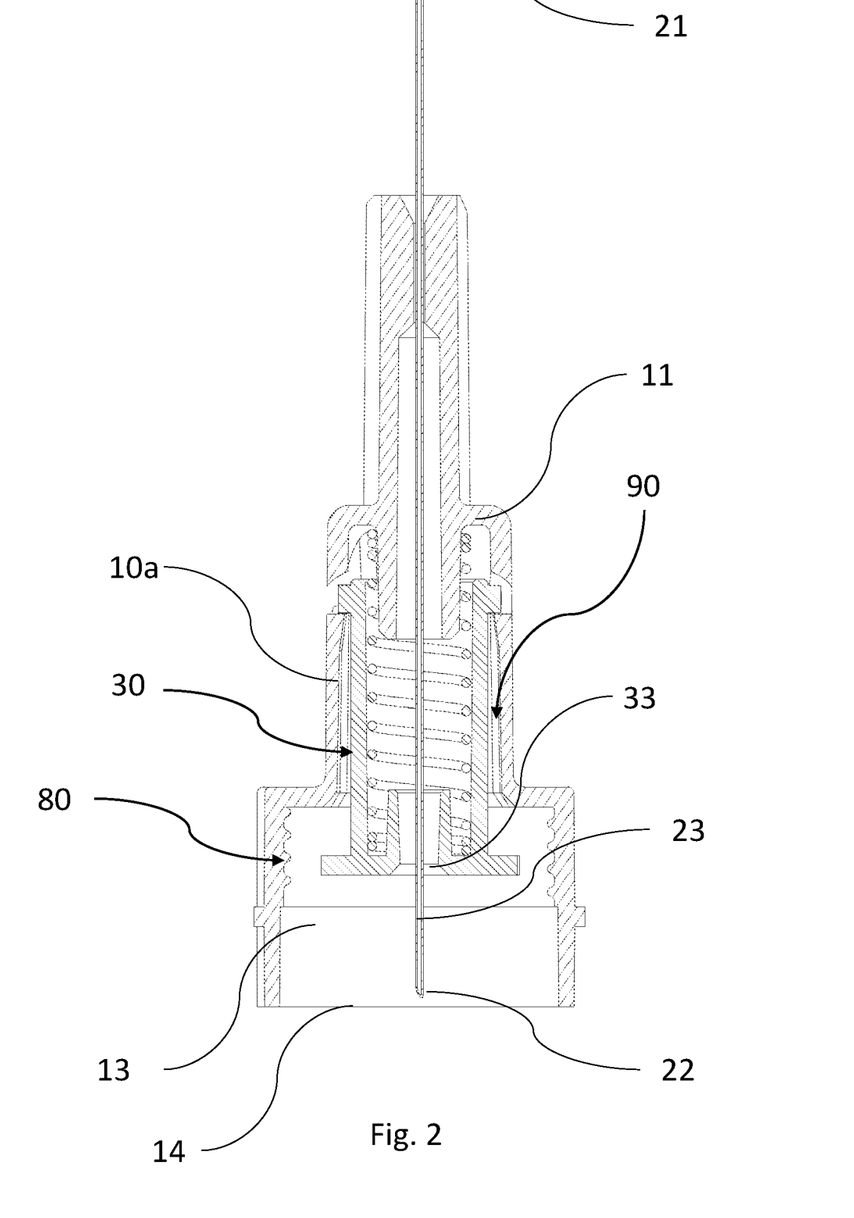
FIG. 2 is a section view of the safety needle device of FIG. 1.
Figure 3:
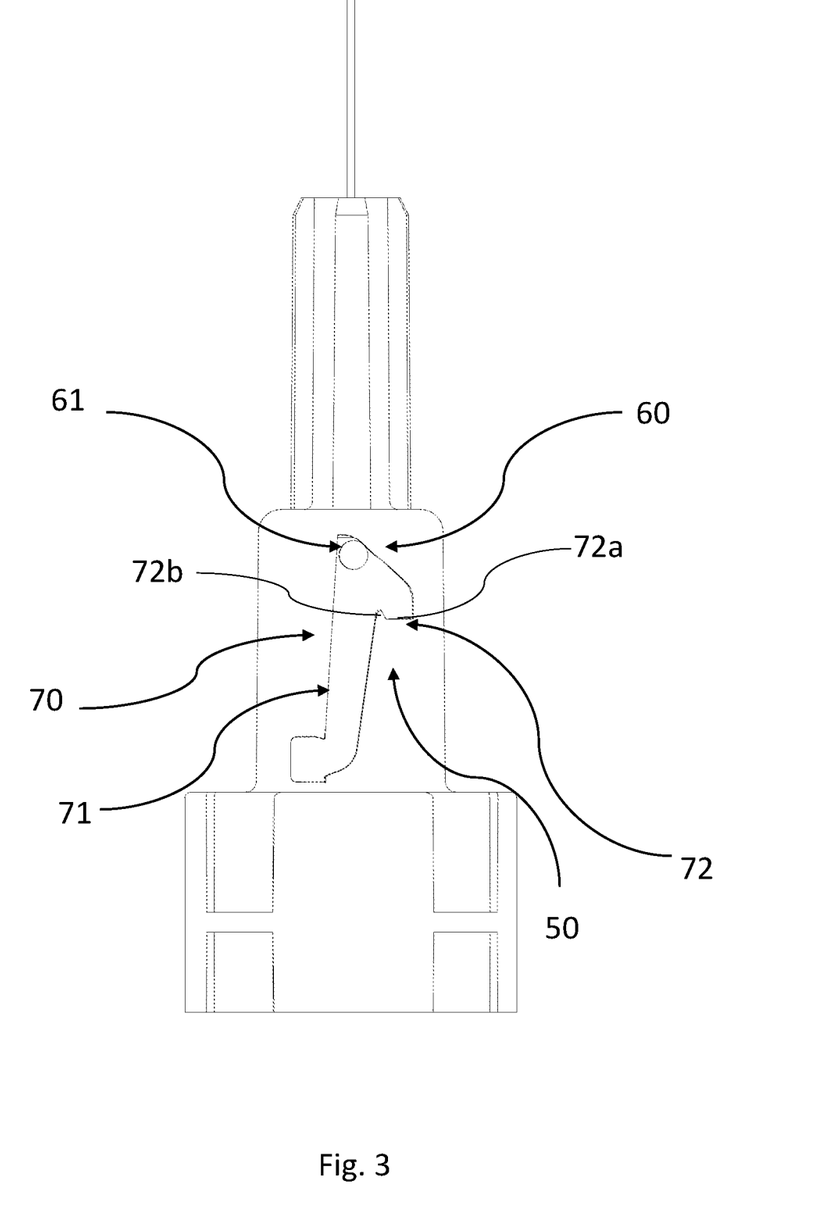
FIG. 3 is a lateral view of the safety needle device according to one embodiment of the present invention, in a use configuration, where some elements are hided to better show other aspects.
Figure 4:
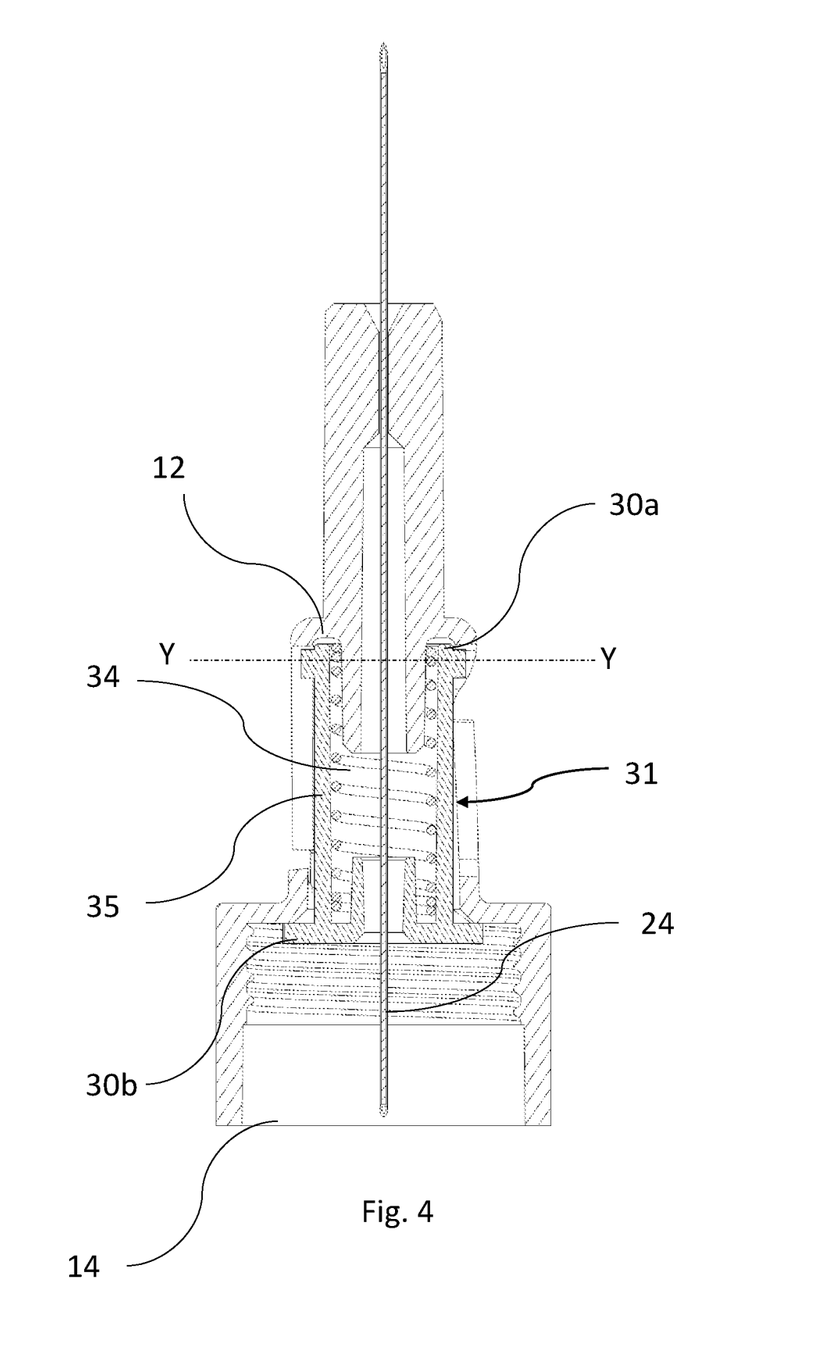
FIG. 4 is a section view of the safety needle device of FIG. 3.
Figure 5:
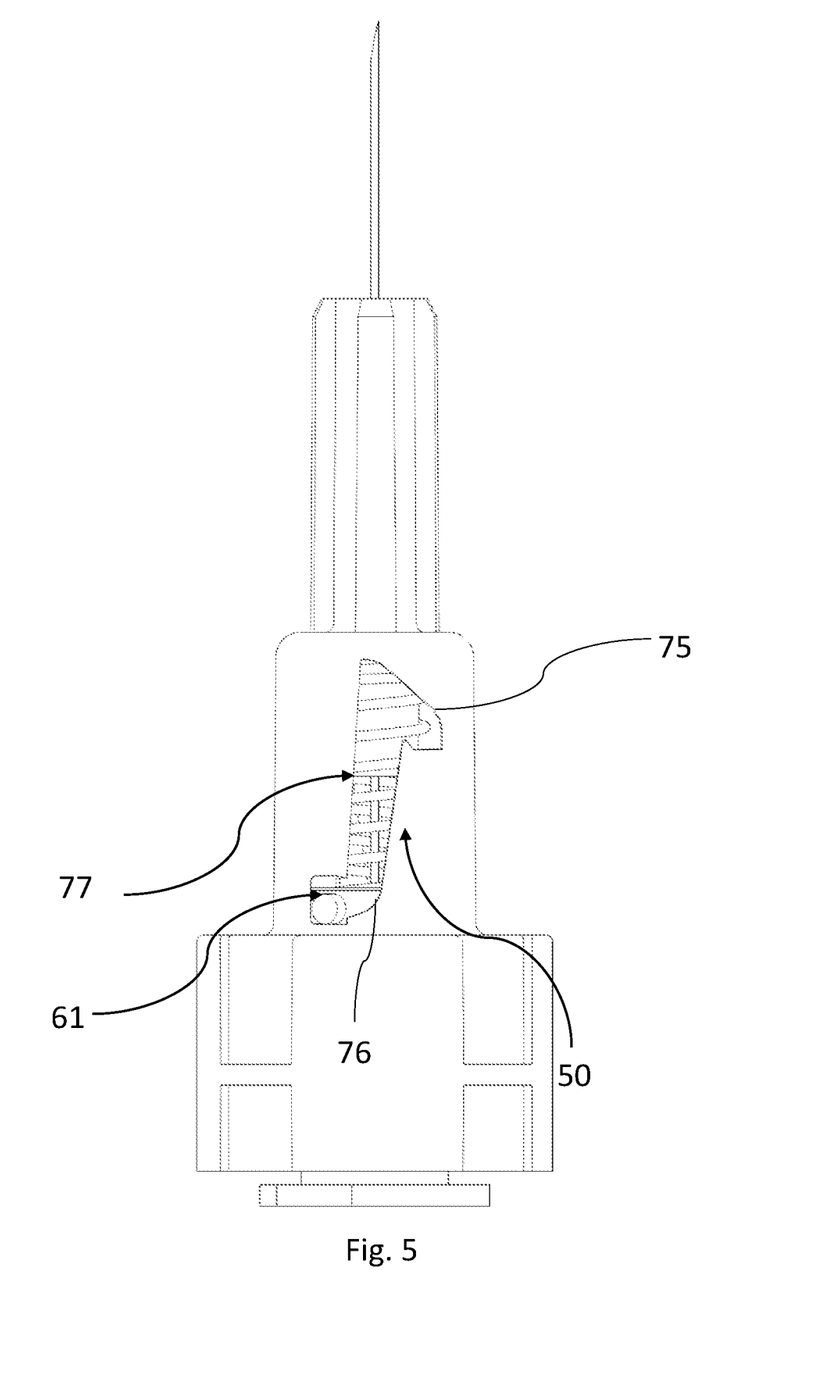
FIG. 5 is a lateral view of the safety needle device according to one embodiment of the present invention, in an after-use configuration, where some elements are hided to better show other aspects.
Figure 6:
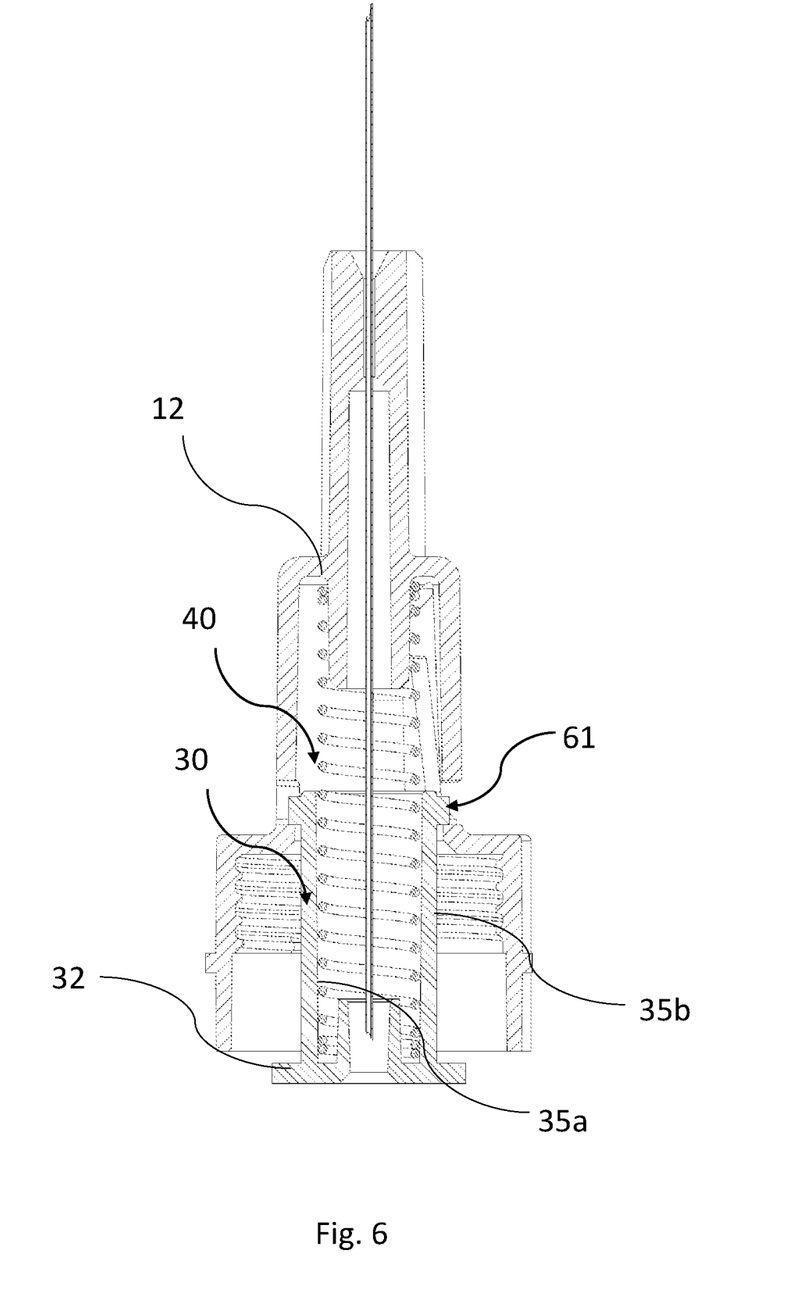
FIG. 6 is a section view of the safety needle device of FIG. 5.
Figure 7:
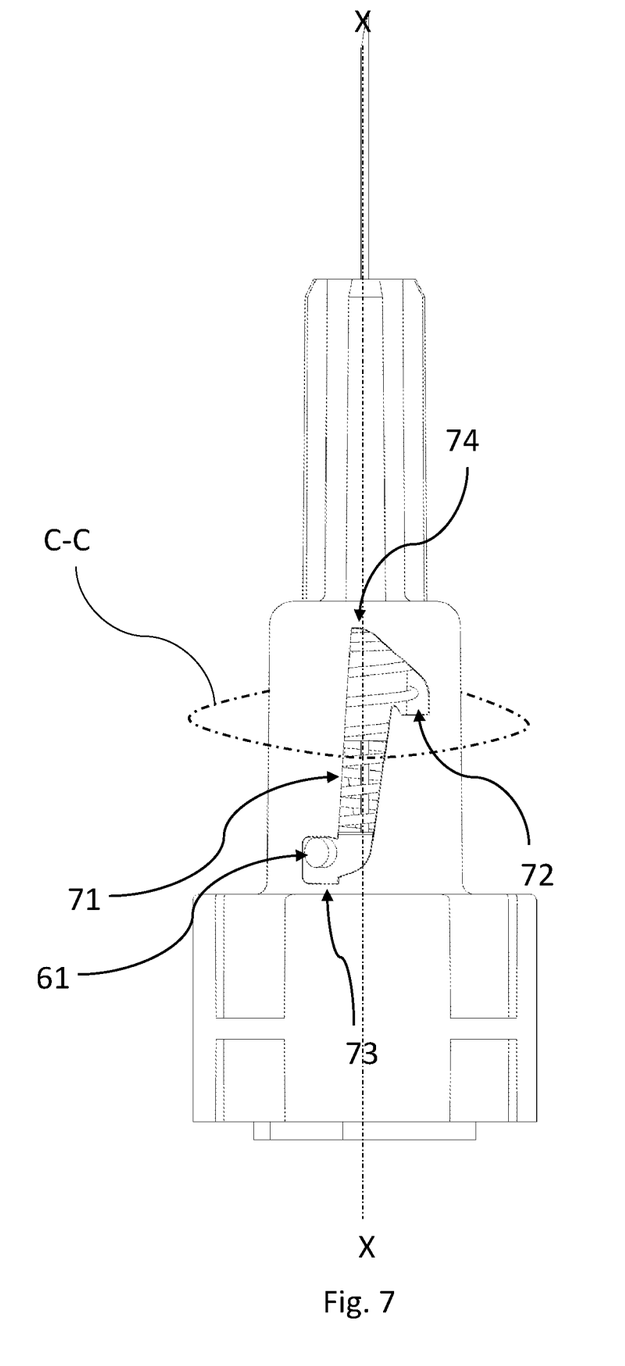
FIG. 7 is a lateral view of the safety needle device according to one embodiment of the present invention, in an locking configuration, where some elements are hided to better show other aspects.

Specifically, the back-end shield 30, as shown in FIG. 2, in the initial position leaves uncovered a first portion 23 of needle 20 arranged inside the cavity 13 and the proximal end 22 of the needle 20. Subsequently, the back-end shield 30, as shown in FIG. 4, in the intermediate position leaves uncovered a second portion 24 of the needle 20 arranged inside the cavity 13 and also the proximal end 22 of the needle 20. It is to be noted that the first portion 23 is shorter than the second portion 24 because the back-end shield 30 has been moved towards the distal end 21 of the needle. Finally, the back-end shield 30, as shown in FIG. 6, in the locking position covers the proximal end 22 of the needle 20. It is worth noting that upon reaching the locking position the back-end shield 30 is configured to cover the proximal end 22 of the needle 20. Optionally, in the locking position a limited sliding the back-end shield 30 along the longitudinal direction X-X is also allowed without uncovering the proximal end 22 of the needle 20, FIGS. 7 and 8.

According to one embodiment, the back-end shield 30 comprises an hallow body 31 extending between a distal portion 30a facing to the upper wall 12 of the hub 10 and a proximal portion 30b facing to the lower aperture 14 of the hub 10. Specifically, the back-end shield 30 is arranged inside the cavity 13 preferably totally in the initial and intermediate position and at least partially in the locking position. The hallow body 31 comprises a lower wall 32 formed at the proximal portion 30b. Such lower wall 32 has an opening 33 which is configured to allow a portion of the needle 20 and the proximal end 22 of the needle 20 to pass through while the back-end shield 30 is moving between the initial position and locking position. The hallow body 31 further comprises a lateral wall 35 extending from the lower wall 32 along the longitudinal direction X-X and defining a passing through channel 34. The passing through channel 34 is configured to house at least partially the needle 20 arranged inside the cavity 13. The lateral wall 35 has an inner surface 35a facing to the passing through channel 34 and an outer surface 35b facing to the cavity 13 of the hub 10.

The safety needle device 1 comprises an elastic member 40 arranged within the cavity 13 and acting between the upper wall 12 and the back-end shield 30 to urge the back-end shield 30 towards the proximal end 21 of the needle 10 along the longitudinal direction X-X. Preferably, the elastic member 40 is configured to constantly urge the back-end shield 30 towards the proximal end 22 of the needle 10. Specifically, the elastic member 40 generates a force directed to the proximal end 22 of the needle 20 as a result of a longitudinal motion of the back-end shield 30 towards the distal end 22 of the needle 20. In detail, the elastic member 40 is configured to be elastically compressed during the coupling of the pen injector with the hub 10, namely during the passage of the back-end shield 30 from the initial position to the intermediate position and to be elastically extended during the removal of the pen injector from the hub 10 with the passage of the back-end shield 30 from the intermediate position to the locking position. In other words, the pen injector acts on the lower wall 32 causing the motion of the back-end shield 30 from the initial position to the intermediate position and then the compression of the elastic member 40. After the removal of the pen injector and its action on the lower wall 32, the back-end shield 30 passes from the intermediate position to the locking position by means of elastic member 40 extension.

Figure 8:
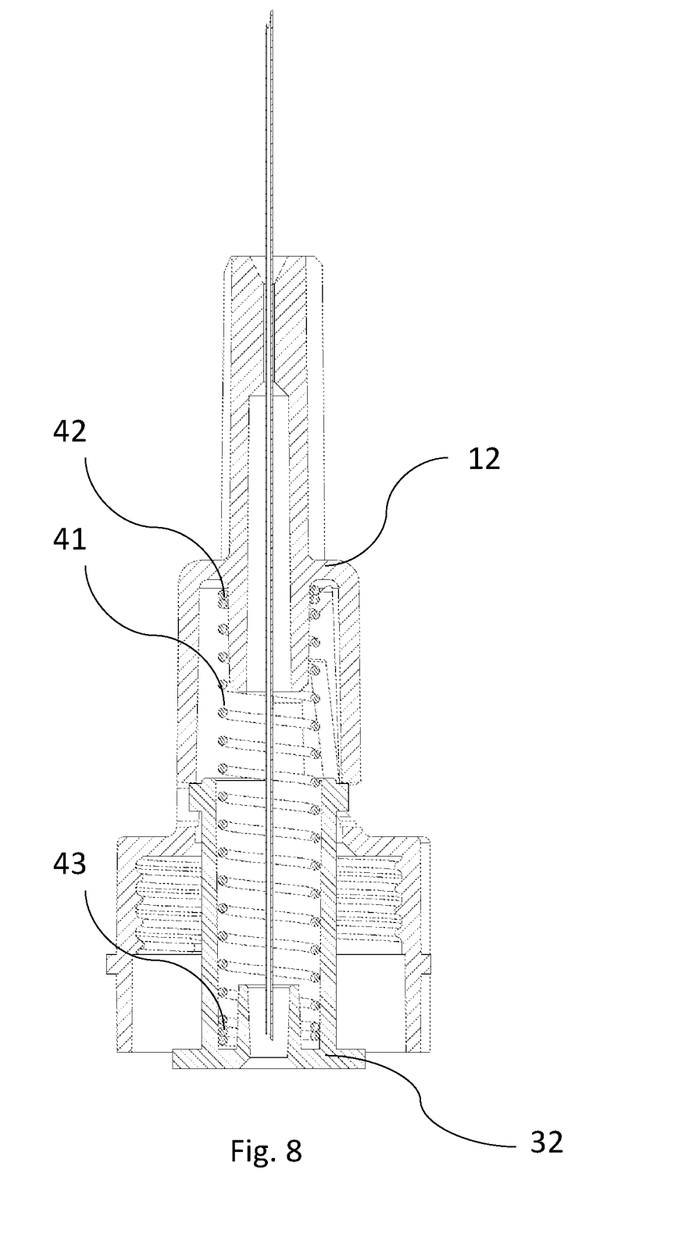
FIG. 8 is a section view of the safety needle device of FIG. 7.

Preferably, the elastic member 40 is interposed between the hub 10 and the back-end shield 30 in order to constantly urge the back-end shield 30. Specifically, the elastic member 40 is at least partially arranged inside the passing through channel 34 which is configured to accommodate a portion of the elastic member 40. It is to be noted that the arrangement of the elastic member 40 inside the passing through channel 34 depends on the position of the back-end shield 30. Namely, in the intermediate position the elastic member 40 is totally arranged in the passing through channel 34 (FIG. 4), while in the initial and locking position the elastic member 40 is partially arranged in the passing through channel 34 (FIGS. 2, 6 and 8).

More preferably, the elastic member 40 is interposed between the upper wall 12 and the lower wall 32 in order to constantly urge the back-end shield 30 towards the proximal end 22.

It is to be noted that, the elastic member 40 surrounds at least partially the needle 20 passing inside the cavity 13 of the hub 10.

According to a preferred embodiment, the elastic member 40 comprises a spring member 41 which extends between a distal portion 42 and a proximal portion 43 along the longitudinal axis X-X. Accordingly, the portion 42 abuts against the upper wall 12 and the proximal portion 43 abuts against the lower wall 32.

According to a preferred embodiment, the hallow body 31 has a tubular shape with a circular cross section.

The safety needle device 1 comprises a locking arrangement 50 configured to guide the back-end shied 30 from the initial position to the locking position and to lock the back-end shield 30 in the locking position. Preferably, the locking arrangement 50 is configured to rotate the back-end shield 30 upon sliding of the back-end shield 30 along the longitudinal direction X-X and to lock the back-end shield 30 in order to constantly cover the proximal end 22 of the needle 20.

The locking arrangement 50 comprises at least a first locking member 60 formed on the back-end shield 30 and at least a second locking member 70 formed on the hub 10. Specifically, the second locking member 70 cooperates with the first locking member 60 to guide the back-end shield 30 from the initial position to the locking position and to lock the back-end shield 30 in the locking position. Preferably, the locking arrangement 50 comprises at least two first locking members 60 and at least two second locking members 70.

The second locking member 70 comprises a passing through guide 71 and the first locking member 60 comprises a protrusion configured to engage the guide 71 and to slide along the passing through guide 71.

According to a preferred embodiment, the protrusion 61 is formed on the outer surface 35b of the back-end shield 30, preferably projecting from the outer surface 35b along a transversal direction Y-Y perpendicular to the outer surface 33b and then to the longitudinal direction X-X. Preferably, the protrusion 61 is formed proximal to the distal portion 30a of the back-end shield 30. More preferably, the locking arrangement 50 comprises at least two protrusions 61 mutually spaced apart along the outer surface 35b of the back-end shield 30. Even more preferably, the two protrusions 61 are circumferentially spaced apart on the back-shield 30. The preferred embodiment shown in the figures, the protrusions 61 are symmetric and circumferentially spaced apart on the outer surface 35b of the back-end shield.

According to a preferred embodiment, the protrusions 61 are pins.

According to one embodiment, the second locking member 70 comprises a passing through guide 71 formed on the lateral wall 11 of the hub 10. Preferably, the passing through guide 71 extends from the inner surface 10a to the outer surface 10b. Specifically, the passing thought guide 71 is an opening formed on the lateral wall 11 of the hub 10. More preferably, the hub 10 comprises two symmetric passing through guides 71 circumferentially spaced apart on the lateral wall 11. In other words, the hub 10 has two passing through guides 71 angularly spaced apart along the lateral wall 11. Such configuration allows to correctly guide the back-end shield 30 between the initial position to the locking position and cooperates with the protrusions to lock the back-end shield 30 in the locking position.

It is to be noted that the passing through guide 71 has a shape shown in FIGS. 1, 3, 5 and 7.

According to a preferred embodiment, the passing through guide 71 comprises a first stopping member 72 and a second stopping member 73.

The first stopping member 72 is configured to engage the protrusion 61 in the initial position of the back-end shield 30 to prevent longitudinal sliding of the back-end shield 30 towards the proximal end 22 of the needle 20. Preferably, the first stopping member 72 comprises a first support portion 72a that retains the protrusion 61 and maintains the back-end shield 30 in the initial position and a second support portion 72b that prevents undesired rotation of the back-end shield 30 about the longitudinal direction X-X. More preferably the second support portion 72a extends along the longitudinal direction X-X from the first support portion 72a towards the distal end 22 of the needle 20. Even more preferably, the first support portion 72a and the second support portion 72b define an initial bay which retains the back-end shield 30 in the initial position until the coupling of the pen injector with the hub 10. As a matter of fact, the first stopping member 72 retains the back-end shield 30 against preloaded elastic force of the elastic member 40 which urges the back-end shield 30 towards the proximal end 22.

The second stopping member 73 is configured to engage the protrusion 61 in the locking position of the back-end shield 30 to prevent longitudinal sliding of the back-end shield 30 both towards the distal end 21 and the proximal end 22 of the needle 10. Specifically, the second stopping member 73 is configured to retain the protrusion 61 in order to prevent further use of the safety needle device 1 and the sliding of the back-end shield along the longitudinal direction X-X. Preferably, the second stopping member 73 comprises a first support portion 73a and a second support portion 73b which prevent the longitudinal sliding of the back-end shield 30 both towards the distal end 21 and the proximal end 22 of the needle. In detail, also the first support portion 73a limits the stroke of the back-end shield 30 along the longitudinal axis X-X retaining the shield 30 against preloaded elastic force of the elastic member 40 which continues to urge the back-end shield 30 towards the proximal end 21 also in the locking position. More preferably, the second stopping member 73 comprises a third support portion 73c and a fourth support portion 73d which prevent rotation of the back-end shield 30 about the longitudinal direction X-X. Specifically, the third support portion 73c extends from the first support portion 73a along the longitudinal direction X-X towards the distal end 21 of the needle 20, while the fourth support portion 73d extends from the second support portion 73a along the longitudinal direction X-X towards the proximal end 22 of the needle 20. Even more preferably, the support portion 73a, 73b, 73c, 74d of the second stopping member 72 defines a locking bay which engages and retains the protrusion 61 when the back-end shield 30 reaches the locking position. In this way the back-end shield is retained in the locking position and the proximal end 22 of the needle is covered after use of the safety needle device.

In other words, the first stopping member 72 and the second stopping member 73 have substantially a "C" shape wherein the "C" of the first stopping is rotated ninety degrees counterclockwise.

According to the preferred embodiment, the first stopping member 72 and the second stopping member 73 are mutually spaced apart along the longitudinal direction X-X. Specifically, the first stopping member 72 is arranged towards the distal end 21 of the needle 20, while the second stopping member 73 is arranged towards the proximal end 22 of the needle 20. In other words, the first stopping member 72 and the second stopping member 73 are offset along the longitudinal direction X-X.

Preferably, the first stopping member 72 and second stopping member 73 are circumferentially spaced apart. More preferably, the first stopping member 72 and second stopping member 73 are spaced apart along a circumferential direction C-C defined around the hub 10.

According to a preferred embodiment, the passing through guide 71 comprises a third stopping member 74 configured to engage the protrusion 61 in the intermediate position to prevent longitudinal sliding of the back-end shield 30 towards the distal end 22 of the needle 20. Preferably, the third stopping member 74 limits the stroke of the protrusion along the longitudinal direction X-X. More preferably, the protrusion 61 abuts against the third stopping member 74 in the intermediate position.

It is to be noted that the third stopping member 74 is spaced apart from the first stopping member 72 along the longitudinal direction X-X towards the distal end 21 of the needle 20. At the same time, the third stopping member 74 is circumferentially spaced apart both from the first stopping member 72 and the second stopping member 73. Preferably, the third stopping member 74 is arranged in the middle between the first stopping member 72 and the second stopping member 73 along the circumferential direction C-C which goes around the hub 10. Instead, the first stopping member 72 is in the middle between the third stopping member 74 and the second stopping member 73 along the longitudinal direction X-X.

According to a preferred embodiment, the passing through guide 71 comprises a guiding portion 77 configured to engage the protrusion 61 and guide the back-end shield 30 from the intermediate position towards the locking position. Preferably, the guiding portion 77 connects the third stopping member 74 to the second stopping member 73 during the passage of the back-end shield from the intermediate position to the final position. The guiding portion 78 is tapered along the longitudinal axis X-X from the distal end 21 to the proximal end 22 of the needle 20.

According to a preferred embodiment, the passing through guide 71 comprises a first rotation member 75 and a second rotation member 76 configured to rotated the back-end shield 30 upon sliding along the longitudinal direction X-X.

The first rotation member 75 is configured to engage the protrusion 61 and to rotate the back-end shield 30 upon sliding of back-end shield 30 along the longitudinal axis X-X from the initial position towards the intermediate position. Preferably the first rotation member 75 is arranged between the first stopping member 72 and the third stopping member 73. More preferably, the first rotation member 75 is arcuate and allows the rotation of the back-end shield 30 during the sliding along the longitudinal direction X-X. the combination of the rotation and the sliding allows the protrusion 61 to get out from the first stopping member 72.

The a second rotation member 76 is configured to engage the protrusion 61 and to rotate the back-end shield 30 upon sliding of the back-end shield 30 along the longitudinal axis X-X from the intermediate position towards the locking position. Preferably the second rotation member 76 is arranged between the third stopping member 72 and the second stopping member 73. More preferably, the second rotation member 76 is arcuate and allows the rotation of the back-end shield 30 during the sliding along the longitudinal direction X-X. The combination of the rotation and the sliding allows the protrusion to engage the second stopping member 72.

According to one embodiment, the hub 10 comprises insertion guides 90 formed on the lateral wall 11 and configured to engage the protrusions 61 during insertion of the back-end shield 30 in the cavity 14 and to guide the protrusion 61 to the passing through guides 71 at the initial position of the back-end shield 30

The invention claimed is:

1. Safety needle device comprising:
    a hub configured to be connected to a pen-injector, the hub comprising a lateral wall and an upper wall which define therebetween a cavity extending between the upper wall and a lower aperture able to receive the pen injector;
    a needle attached to the hub, the needle extending along a longitudinal direction between a distal end, configured for insertion into a patient, and an opposed proximal end configured to be connected to the pen injector,
    a back-end shield slidable along the longitudinal direction within the cavity of the hub and rotatable about the longitudinal direction, the back-end shield being movable irreversibly from an initial position, before connection of the pen injector to the hub, to a locking position, after removal of the pen injector to the hub passing through an intermediate position,
    an elastic member arranged within the cavity and acting between the upper wall and the back-end shield to urge the back-end shield towards the proximal end of the needle along the longitudinal direction,
    a locking arrangement comprising at least a first locking member formed on the back-end shield and at least a second locking member formed on the hub, the second locking member cooperating with the first locking member to guide the back-end shield from the initial position to the locking position and to lock the back-end shield in the locking position,
    the second locking member comprises a passing through guide formed on the lateral wall of the hub;
    the first locking member comprises a protrusion configured to engage the guide and to slide along the guide;
    wherein the passing through guide comprises:
        a first stopping member configured to engage the protrusion in the initial position of the back-end shield to prevent longitudinal sliding of the back-end shield towards the proximal end of the needle;
        a second stopping member configured to engage the protrusion in the locking position of the back-end shield to prevent longitudinal sliding of the back-end shield both towards the distal end and the proximal end of the needle;
    the back-end shield in the initial position leaves uncovered a first portion of needle arranged inside the cavity and the proximal end of the needle;
    the back-end shield in the intermediate position leaves uncovered a second portion of the needle arranged inside the cavity and the proximal end of the needle, the first portion being shorter than the second portion;
    the back-end shield in the locking position covers the proximal end of the needle.

2. The safety needle device according to claim 1, wherein:
    the hub has an inner surface facing to the cavity and opposed outer surface;
    the passing through guide extends from the inner surface to the outer surface.

3. The safety needle device according to claim 1, wherein:
    the first stopping member and the second stopping member are mutually spaced apart along the longitudinal direction;
    the first stopping member is arranged towards the distal end of the needle;
    the second stopping member is arranged towards the proximal end of the needle.

4. The safety needle device according to claim 1, wherein the passing through guide comprises:
    a third stopping member configured to engage the protrusion in the intermediate position to prevent longitudinal sliding of the back-end shield towards the distal end of the needle;
    the third stopping member being spaced apart from the first stopping member along the longitudinal direction towards the distal end of the needle.

5. The safety needle device according to claim 1, wherein the passing through guide comprises:
    a guiding portion configured to engage the protrusion and guide the back-end shield from the intermediate position towards the locking position;
    the guiding portion being tapered along the longitudinal axis from the distal end to the proximal end of the needle.

6. The safety needle device according to claim 1, wherein the passing through guide comprises:
    a first rotation member configured to engage the protrusion and to rotate the back-end shield upon sliding of back-end shield along the longitudinal axis from the initial position towards the intermediate position;
    a second rotation member configured to engage the protrusion and to rotate the back-end shield upon sliding of the back-end shield along the longitudinal axis from the intermediate position towards the locking position.

7. The safety needle device according to claim 1, wherein the back-end shield comprises a hollow body extending between a distal portion facing to the upper wall of the hub and a proximal portion facing to the lower aperture of the hub; the hollow body comprising:
    lower wall formed at the proximal portion and having an opening configured to allow a portion of the needle and the proximal end of the needle to pass upon moving of the back-end shield between the initial position and locking position;
a lateral wall extending from the lower wall along the longitudinal axis and defining a passing through channel configured to house at least partially the needle.

8. The safety needle device according to claim 7, wherein the lateral wall has a inner surface facing to the passing through channel and an outer surface facing to the cavity of the hub and the protrusions are formed on the outer surface of the back-end shield.

9. The safety needle device according to claim 7, wherein:
the elastic member is interposed between the upper wall of the hub and the lower wall of the back-end shield;
the elastic member surrounds at least partially the needle passing inside the cavity of the hub.

10. The safety needle device according to claim 1, wherein the protrusions are pins.

11. The safety needle device according to claim 1, wherein the elastic member comprises a spring element extending between a distal portion and a proximal portion along the longitudinal axis.

12. The safety needle device according to claim 1, wherein
the hub comprises two symmetric passing through guides circumferentially spaced apart on the lateral wall;
the back-end shield comprises two symmetric protrusions circumferentially spaced apart on the back-end shield.

13. The safety needle device according to claim 1, wherein the hub comprises insertion guides formed on the lateral wall and configured to engage the protrusions during insertion of the back-end shield in the cavity and to guide the protrusion to the passing through guides at the initial position of the back-end shield.

* * * * *